United States Patent
Sackellares et al.

(10) Patent No.: US 8,204,583 B2
(45) Date of Patent: Jun. 19, 2012

(54) SYSTEM FOR SEIZURE MONITORING AND DETECTION

(75) Inventors: J. Chris Sackellares, Gainesville, FL (US); Shiau Deng-Shan, Gainesville, FL (US)

(73) Assignee: Optima Neuroscience, Inc., Alachua, FL (US)

( * ) Notice: Subject to any disclaimer, the term of this patent is extended or adjusted under 35 U.S.C. 154(b) by 876 days.

(21) Appl. No.: 12/288,834

(22) Filed: Oct. 23, 2008

(65) Prior Publication Data

US 2009/0124923 A1    May 14, 2009

Related U.S. Application Data (60) Provisional application No. 60/960,980, filed on Oct. 23, 2007.

(51) Int. Cl.
*A61B 5/04* (2006.01)
(52) U.S. Cl. ........................ 600/544; 600/545
(58) Field of Classification Search .......... 600/300–301, 600/544–545
See application file for complete search history.

(56) References Cited

U.S. PATENT DOCUMENTS

| | | | |
|---|---|---|---|
| 5,269,302 A | 12/1993 | Swartz et al. | |
| 5,713,923 A | 2/1998 | Ward et al. | |
| 5,743,860 A * | 4/1998 | Hively et al. | 600/544 |
| 5,978,702 A | 11/1999 | Ward et al. | |
| 6,134,474 A | 10/2000 | Fischell et al. | |
| 6,304,775 B1 * | 10/2001 | Iasemidis et al. | 600/544 |
| 6,442,421 B1 | 8/2002 | Le Van Quyen et al. | |
| 6,466,822 B1 | 10/2002 | Pless | |
| 6,473,639 B1 | 10/2002 | Fischell et al. | |
| 6,497,699 B1 | 12/2002 | Ludvig et al. | |
| 6,507,754 B2 | 1/2003 | Le Van Quyen et al. | |
| 6,671,555 B2 | 12/2003 | Gielen et al. | |
| 6,678,548 B1 | 1/2004 | Echauz et al. | |
| 6,690,974 B2 | 2/2004 | Archer et al. | |
| 6,735,467 B2 | 5/2004 | Wilson | |
| 6,788,975 B1 | 9/2004 | Whitehurst et al. | |
| 6,793,670 B2 | 9/2004 | Osorio et al. | |
| 6,944,501 B1 | 9/2005 | Pless | |
| 7,003,352 B1 | 2/2006 | Whitehurst | |
| 7,006,872 B2 | 2/2006 | Gielen et al. | |
| 7,054,414 B2 | 5/2006 | Bergman et al. | |
| 7,204,833 B1 | 4/2007 | Osorio et al. | |

(Continued)

FOREIGN PATENT DOCUMENTS

WO    WO-2004036804    4/2004

(Continued)

OTHER PUBLICATIONS

WO-ISR for PCT/US2006/048031, Oct. 5, 2008, University of Florida.

(Continued)

*Primary Examiner* — Miranda Le
*Assistant Examiner* — Tiffany Weston
(74) *Attorney, Agent, or Firm* — Edwards Wildman Palmer LLP; George N. Chaclas

(57) ABSTRACT

Systems and methods for the detection of pathological conditions in a brain analyze signal properties of the brain electrical activity recordings. The pathological conditions to be detected include the occurrence of a seizure event. The systems and methods calculate a seizure susceptibility index (SSI) for real time brain function monitoring and for a pre-screening process of seizure detection.

37 Claims, 6 Drawing Sheets

U.S. PATENT DOCUMENTS

| | | | |
|---|---|---|---|
| 7,263,467 | B2 | 8/2007 | Sackellares et al. |
| 7,269,455 | B2 | 9/2007 | Pineda |
| 7,373,199 | B2 | 5/2008 | Sackellares et al. |
| 7,433,732 | B1* | 10/2008 | Carney et al. .............. 600/544 |
| 2002/0072770 | A1 | 6/2002 | Pless |
| 2002/0077670 | A1 | 6/2002 | Archer et al. |
| 2002/0103512 | A1 | 8/2002 | Echauz et al. |
| 2003/0083716 | A1 | 5/2003 | Nicolelis et al. |
| 2003/0158587 | A1 | 8/2003 | Esteller et al. |
| 2003/0186942 | A1 | 10/2003 | Crooks et al. |
| 2004/0068199 | A1 | 4/2004 | Echauz et al. |
| 2004/0082984 | A1 | 4/2004 | Osorio et al. |
| 2004/0122335 | A1 | 6/2004 | Sackellares et al. |
| 2004/0127810 | A1 | 7/2004 | Sackellares et al. |
| 2004/0266737 | A1 | 12/2004 | Crooks et al. |
| 2005/0182453 | A1 | 8/2005 | Whitehurst et al. |
| 2005/0240242 | A1 | 10/2005 | DiLorenzo |
| 2006/0111644 | A1 | 5/2006 | Guttag et al. |
| 2006/0173510 | A1 | 8/2006 | Besio et al. |
| 2006/0287607 | A1 | 12/2006 | Sackellares et al. |
| 2007/0016094 | A1 | 1/2007 | Pless |
| 2007/0150024 | A1 | 6/2007 | Leyde et al. |
| 2007/0197930 | A1 | 8/2007 | Sarkela |
| 2007/0213786 | A1* | 9/2007 | Sackellares et al. ............ 607/45 |
| 2007/0244408 | A1 | 10/2007 | Wingeier et al. |
| 2007/0250133 | A1 | 10/2007 | Carlson et al. |
| 2008/0021340 | A1 | 1/2008 | Sarkela |
| 2008/0082019 | A1 | 4/2008 | Ludving et al. |
| 2008/0146958 | A1 | 6/2008 | Guillory et al. |

FOREIGN PATENT DOCUMENTS

| | | |
|---|---|---|
| WO | WO-2004078252 | 9/2004 |
| WO | WO-2005117693 | 12/2005 |

OTHER PUBLICATIONS

WO-Writ, Opinion PCT/US06/048031, Oct. 5, 2008, University of Florida.

K Lehnertz, et al., "Can Epileptic Seizures Be Predicted? Evidence from Nonlinear Time Series Analysis of Brain Electrical Activity"; Physical Review Letters, vol. 80, No. 22, pp. 5019-5022, Jun. 1, 1998.

M. Le Van Quyen, et al., "Spatio-Temporal Distribution of the Dynamical Pre-Ictal Changes Detected by Non Linear Analysis of Intracerebral EEG" Epilspsia, vol. 40, Suppl. 7, An 3.012, pp. 168, 1999.

M. Le Van Quyen, et al., "Evidence of Pre-Seizure Changes on Scalp EEG Recordings by Non Linear Analysis", Epilspsia, vol. 40, Suppl. 7, AN 3.036, pp. 174, 1999.

L.D. Iasemidis, et al., "The Evolution With Time of the Spatial Distribution of the Largest Lyapunov Exponent on the Human Epileptic Cortex"; Singapore Word Scientific, pp. 49-82, 1991.

J. Martinerie et al., "Epileptic Seizures can be anticipated by non-linear analysis", Oct. 1998, Nature Medicine vol. 4 pp. 1173-1176.

Iasemidis LD, et al., "Adaptive epileptic seizure prediction system"; IEEE Transactions on Biomedical Engineering 50(5): 616-627, 2003.

Sackellares JC, et al., "Predictability Analysis for an Automated Seizure Prediction Algorithm"; Journal of Clinical Neurophysiology, 23 (6): 509-520, 2006.

Iasemidis, Leonidas D., et al., The evolution with time of the spatial distribution of the largest Lyapunov exponent on the human epileptic cortex, Proceedings of the Conference on Measuring Chaos in the Human Brain, Apr. 3-5, 1991, World Scientific Publishing Co. Pte. Ltd., pp. 49-82.

Saab M.E. et al. A system to detect the onset of epileptic seizures in scalp EEG. Clinical Neurophysiology 116 (2005) 427-442.

Hopfengartner R., et al. An efficient, robust and fast method for the offline detection of epileptic seizures in long-term scalp EEG recordings. Clinical Neurophysiology 118 (2007) 2332-2343.

McSharry, P.E., et al. Linear and non-linear methods for automatic seizure detection in scalp electro-encephalogram recordings. Med. Biol. Eng. Comput., 2002, 40, 447-461.

van Putten, Michael J.A.M., et al. Detecting temporal lobe seizures from scalp EEG recordings: A comparison of various features. Clinical Neurophysiology 116 (2005) 2480-2489.

Wilson, Scott B., et al. Seizure detection: evaluation of the Reveal algorithm. Clinical Neurophysiology 115 (2004) 2280-2291.

Wilson, Scott B. A neural network method for automatic and incremental learning applied to patient-dependent seizure detection. Clinical Neurophysiology 116 (2005) 1785-1795.

Wilson, Scott B. Algorithm architectures for patient dependent seizure detection. Clinical Neurophysiology 117 (2006) 1204-1216.

Nair, Sandeep P., et al., Effects of Acute Hippocampal Stimulation on EEG Dynamics. Proceedings of the 28th IEEE, EMBS Annual International Conference, New York, NY, Aug. 30-Sep. 3, 2006, pp. 4382-4386.

WO-International Preliminary Report on Patentability for PCT/US2008/012071, Apr. 27, 2010, Optima Neuroscience, Inc.

WO-Written Opinion for PCT/US2008/012071, Dec. 22, 2010, Optima Neuroscience, Inc.

* cited by examiner

SYSTEM FOR SEIZURE MONITORING AND DETECTION

CROSS-REFERENCE TO RELATED APPLICATION

This application claims priority to U.S. Provisional Patent Application No. 60/960,980, filed Oct. 23, 2007, which is incorporated herein by reference.

BACKGROUND OF THE SUBJECT TECHNOLOGY

1. Field of the Subject Technology

The present subject technology relates to the use of advanced linear and nonlinear signal analysis for the detection of seizures and the interpretation of critical neurological conditions in the brain's electrical activity, such as the Electroencephalogram (EEG).

2. Background Art

Epilepsy is a condition characterized by recurrent seizures which are the outward manifestation of excessive or hypersynchronous abnormal electrical activity of neurons in the cerebral cortex of the brain. A seizure patient may suffer from several different types of seizures, or any combination thereof. For example, a common type of epilepsy is called the grand mal seizure, which is manifested by symptoms of convulsions with tonic-clonic contractions of muscles. Another type of epilepsy is called the absence seizure, which is characterized by brief and sudden loss of consciousness. Other types of seizures include complex partial seizure, which is characterized by a complete loss of consciousness, and psychomotor seizure, which is characterized by clouding of consciousness for one to two minutes. Some types of seizures may involve the entire brain, while other types of seizures may affect only a local portion of the brain.

Figure 3A:
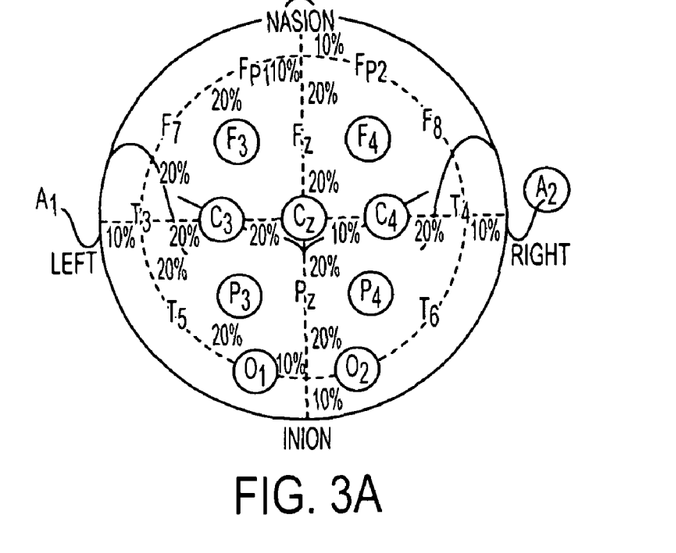
FIG. 3A illustrates a side view of a person with a typical arrangement of electrodes positioned on the scalp of an epilepsy patient.
Figure 3B:
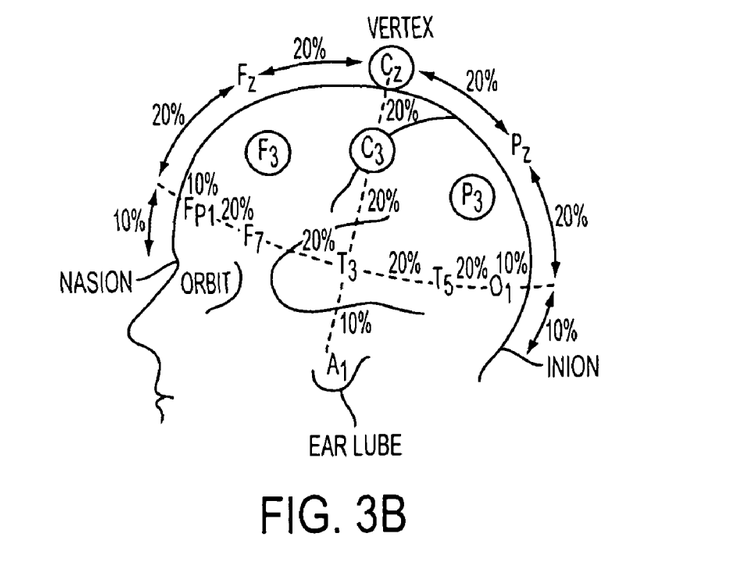
FIG. 3B illustrates a top view of a person with a typical arrangement of electrodes positioned on the scalp of an epilepsy patient.

EEGs have been employed to record electrical signals generated by different parts of the brain. In a typical EEG, a plurality of electrodes are placed across the scalp of a patient with predetermined spacing. FIGS. 3A and 3B show diagrams illustrating a typical arrangement of electrodes positioned on the scalp of an epilepsy patient along standard lines of measurements. The voltage waveform across a given pair of electrodes in the montage of an EEG recording is commonly referred to as a channel. A seizure is typically manifested by a highly rhythmic pattern of voltage waveforms on an EEG recording. However, depending upon the individual patient, different types of seizures, and various other factors, detection of an onset of seizure is sometimes not readily discernable by a human reader from a montage of an EEG recording. For example, sometimes a seizure may manifest itself as a random waveform pattern across a montage of an EEG recording. Sometimes recording errors may occur in one or more channels of a montage of an EEG recording. Sometimes an onset of seizure is not shown on an EEG recording as a rhythmic pattern of waveforms, but rather as an abnormal change from the background waveform pattern.

A system that is able to provide a real time quantitative seizure susceptibility index and seizure detection can be very useful clinically. A clinical implementation of such a system can be utilized immediately in a variety of hospital settings to improve patient safety, reduce staffing requirements, time doses of anticonvulsants, and to time ictal diagnostic procedures. Venues for the application include specialized emergency medical units (EMUs), intensive care units (ICUs), recovery rooms, and emergency treatment areas. However, in addition to inpatient monitoring applications, other monitoring applications such as use of the software in ambulatory recording devices may develop in the future.

A human reader of an EEG recording may need to go through hours or even days of recorded waveforms to determine the onset, duration, and type of seizures that may have occurred during that time. The human reader may miss an occurrence of a seizure, which is referred to as a false negative, or may mark a non-seizure segment of the waveforms as a seizure event, which is referred to as a false positive.

Conventional algorithms have been developed to assist a human reader in detecting seizures using traditional fast Fourier transform (FFT) or other spectral analysis techniques such as wavelet analysis. While these traditional techniques are usually effective in detecting highly rhythmic patterns of waveforms in order to identify a seizure event, some types of seizures which are not manifested by such highly rhythmic patterns may still be missed. Signal processing using conventional spectral analysis techniques may also sometimes return very high false positives, depending upon the parameters set by the algorithm.

Several U.S. patents and patent applications have pursued advancement of analysis. For example, U.S. Pat. No. 6,304,775 issued on Oct. 16, 2001, U.S. Pat. No. 7,263,467 issued Aug. 28, 2007, and U.S. Pat. No. 7,373,199 issued May 13, 2008, each of which is incorporated herein by reference, has advanced the technology. U.S. Patent Application Publication No. 2006/0287607 published on Dec. 21, 2006, which is incorporated herein by reference, has also advanced the technology.

SUMMARY

In view of the above, there is a need for an improved system and method for detecting seizures from EEG recordings with a high degree of reliability. The subject technology relates to a system designed for a seizure monitoring and detection system (SMDS) that incorporates a seizure susceptibility index (SSI) and a seizure detection algorithm. The seizure detection algorithm utilizes the linear and nonlinear characteristics of the EEG signals, where nonlinear features are used for detection of events and linear features are used for rejections of recording artifacts and normal physiological activities (for example, sleep, muscle activity, chewing, etc). The SMDS not only can detect seizure events, but also can recognize the EEG seizure onset types (i.e., left-unilateral, right-unilateral or bilateral). The SSI is a continuous indicator of the likelihood of a seizure occurrence based on a developed Automated Dynamical Seizure Warning Algorithm (ADSWA).

The ADSWA uses algorithms that detect spatiotemporal patterns of quantitative dynamical descriptors derived from EEG signals. The spatiotemporal patterns characterize the pre-seizure (preictal) and seizure (ictal) states. The SMDS is designed to be placed at the bedside to monitor the EEG and to provide medical staff information as to the likelihood of an ensuing seizure and to alert the staff when seizures occur. SMDS can also be used as post hoc EEG review software that could enhance the efficiency of the review process by technicians and electroencephalographers.

One object is to develop a SMDS that, although based on sophisticated and cutting edge approaches to signal analysis, provides simple and intuitive on line real time output that is useful at the bedside to medical and nursing personnel who are not expert in interpreting EEG recordings. The SMDS may also provide a storage function to allow subsequent review and interpretation by expert electroencephalographers. Thus, one embodiment will provide bedside monitoring and alert functions and data selection and data reduction functions to facilitate off-line review and analysis of the EEG. The SMDS may be further operative to work with existing EEG acquisition systems. By identifying seizure activity, trained neurologists can advantageously focus their attention on the relevant data segments rather than having to review all the data.

In one embodiment, the subject technology is directed to a system for monitoring brain pathological conditions of a patient in real time from a series of analyses on scalp or intracranial brain electrical activity, such as multi-channel EEG signals. The system includes an amplifier configured to receive and amplify the EEG signals, an analog-to-digital multi-converter configured to convert the EEG signals into digital signals, and a signal processor configured to process the digital signals and to provide outputs indicative of the brain pathological conditions. The processor is programmed to perform analyses for each EEG channel including filtering signals in a first frequency range A and a second frequency range B, each frequency range including a plurality of segments. For each segment in the first frequency range A, the processor calculates: nonlinear EEG descriptors that extract signal characteristics, wherein the nonlinear EEG descriptors include short-term maximum Lyapunov exponent (STLmax) and pattern match regularity statistic (PMRS-A) and additionally include descriptors selected from the group consisting of complexity, stationarity, chaoticity, regularity, and combinations thereof; a convergence measure of the nonlinear EEG descriptors among selected EEG channels for each sequential segment; and a seizure susceptibility index (SSI) based on a distribution of STLmax, PMRS, T-index$_1$, and T-index$_2$ outputs. The processor also determines whether an impending seizure is susceptible based on SSI values. When the impending seizure is indicated, the processor performs the following: i) for each segment in the second frequency range B, calculate a pattern match regularity statistic (PMRS-B) for each of the EEG channels; ii) for each segment in the second frequency range B, calculate the standard deviation of the signal amplitude (STD) for each of the EEG channels; iii) for each segment in the second frequency range B, calculate a maximum and minimum one second standard deviation of a signal amplitude (STX and STM) for each of the EEG channels; iv) for each segment in the second frequency range B, calculate a maximum one-second negative-to-positive zero-crossing frequency, where each one second signal is normalized to have mean zero (ZCmax) for each of the EEG channels; v) for sequential EEG segments, calculate the maximum amplitude difference between a low and a high frequency band (DAmp) for each of the EEG channels; and vi) determine whether a seizure event is occurring based on the spatio-temporal structure of PMRS-B, STD, STX, STM, DAmp, and ZCmax outputs.

It should be appreciated that the subject technology can be implemented and utilized in numerous ways, including without limitation as a process, an apparatus, a system, a device, a method for applications now known and later developed, or a computer-readable medium. These and other unique features of the system disclosed herein will become more readily apparent from the following description and the accompanying drawings.

BRIEF DESCRIPTION OF THE DRAWINGS

The present subject technology will be described with particular embodiments thereof, and references will be made to the drawings in which.

DETAILED DESCRIPTION

The present invention overcomes many of the prior art problems associated with monitoring seizure activity and determining when seizures occur. The advantages, and other features of the systems and methods disclosed herein, will become more readily apparent to those having ordinary skill in the art from the following detailed description of certain preferred embodiments taken in conjunction with the drawings which set forth representative embodiments of the present invention.

Figure 1:
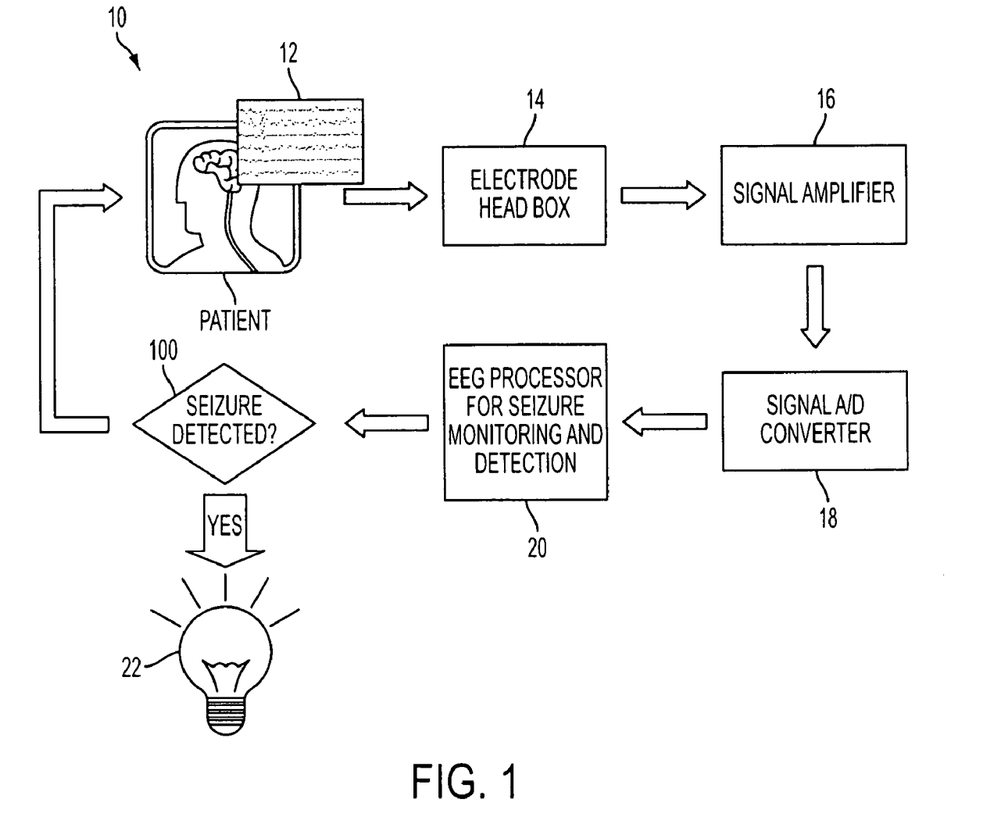
FIG. 1 illustrates a schematic diagram of a real-time seizure monitoring and detection system in accordance with the subject technology.

Referring to FIG. 1, a schematic diagram of a real-time seizure monitoring and detection system (SMDS) 10 in accordance with the subject technology is shown. The SMDS 10 has electrodes (not explicitly shown) for capturing electrical signals 12 from the patient's brain in a known manner. It is envisioned that the electrodes would be placed on the patient's head according to the international 10-20 system shown in FIGS. 3A and 3B.

In FIG. 3A, a top view is shown and a left side view of the patient's head is shown in FIG. 3B. In the international 10-20 system, "A" denotes an ear lobe location, "C" denotes a central location, "Pg" denotes a nasopharyngeal location, "P" denotes a parietal location, "F" denotes a frontal location, "Fp" denotes a frontal polar location, and "O" denotes an occipital location as shown. Alternatively, an intracranial EEG may also be used to generate the electrical signals 12 as opposed to the scalp version of FIGS. 3A and 3B. In other embodiments, the EEG signal can be derived from intracranial electrodes placed on the surface of the brain (subdural electrodes) or inserted into brain tissue.

Figure 4:
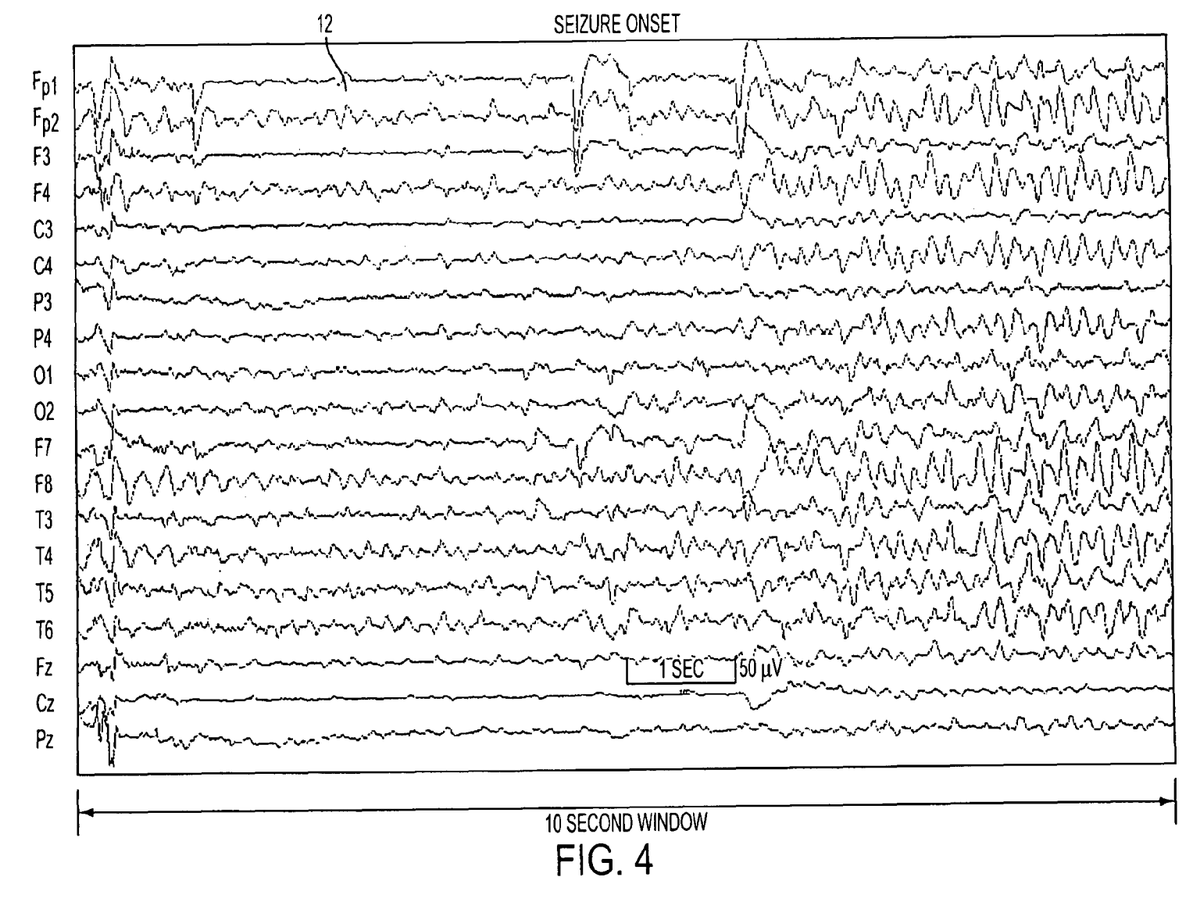
FIG. 4 illustrates a typical referencing montage in accordance with the subject technology.

Referring now to FIG. 4, a typical referencing montage 12 generated by connecting the SMDS 10 to a scalp, for example, as shown in FIGS. 3A and 3B is shown. An EEG recording typically includes a plurality of voltage waveforms recorded simultaneously across a plurality of predetermined pairs of electrodes. A simultaneous recording of such multiple waveforms across multiple electrodes is commonly referred to as a montage. The waveform measured across each designated electrodes for indicating activity in a given region of the brain is commonly referred to as a channel. The montage 12 of FIG. 4 illustrates a typical referential montage of a scalp EEG recording with nineteen channels of simultaneous waveforms recorded over a ten second duration.

Referring again to FIG. 1, the electrodes connect to an electrode head box 14 that transmits the electrical signals 12 to a signal amplifier 16. The signal amplifier 16 increases the signal strength without inducing undesirable noise. The amplified analog electrical signals pass to an analog to digital converter 18 for conversion into digital signals.

The digital signals are evaluated by an EEG processor 20 to determine if the patient is experiencing seizure activity as described in detail below. The EEG processor 20 runs a monitoring and detection process 100 as described below with respect to FIG. 6. If the SMDS 10 is being used for real-time seizure monitoring and seizure activity is detected, the SMDS 10 will provide notification such as by an alarm 22 or other like means.

Figure 2:
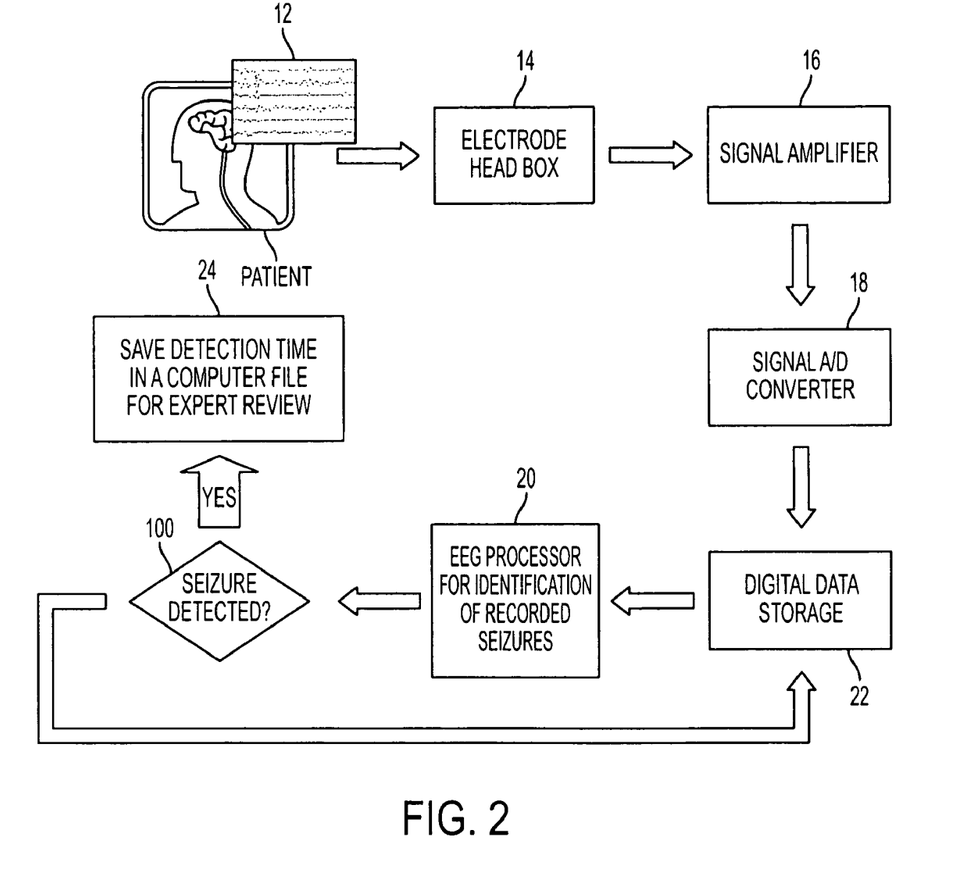
FIG. 2 illustrates a schematic diagram of using a seizure monitoring and detection system for post hoc seizure review in accordance with the subject technology.

Referring now to FIG. 2, the SMDS 10 uses additional hardware to perform post-seizure review in accordance with the subject technology. The SMDS 10 stores the amplified digital signals in a digital data storage device 22 such as a hard drive. At a subsequent time of the user's choosing, the EEG processor 20 may analyze the stored signals using the method 100 to identify seizure activity. At the points where seizure activity occurred, the EEG processor 20 can note the temporal location in a memory file 24 for investigation by an expert, further SMDS analysis, and the like.

Figure 5:
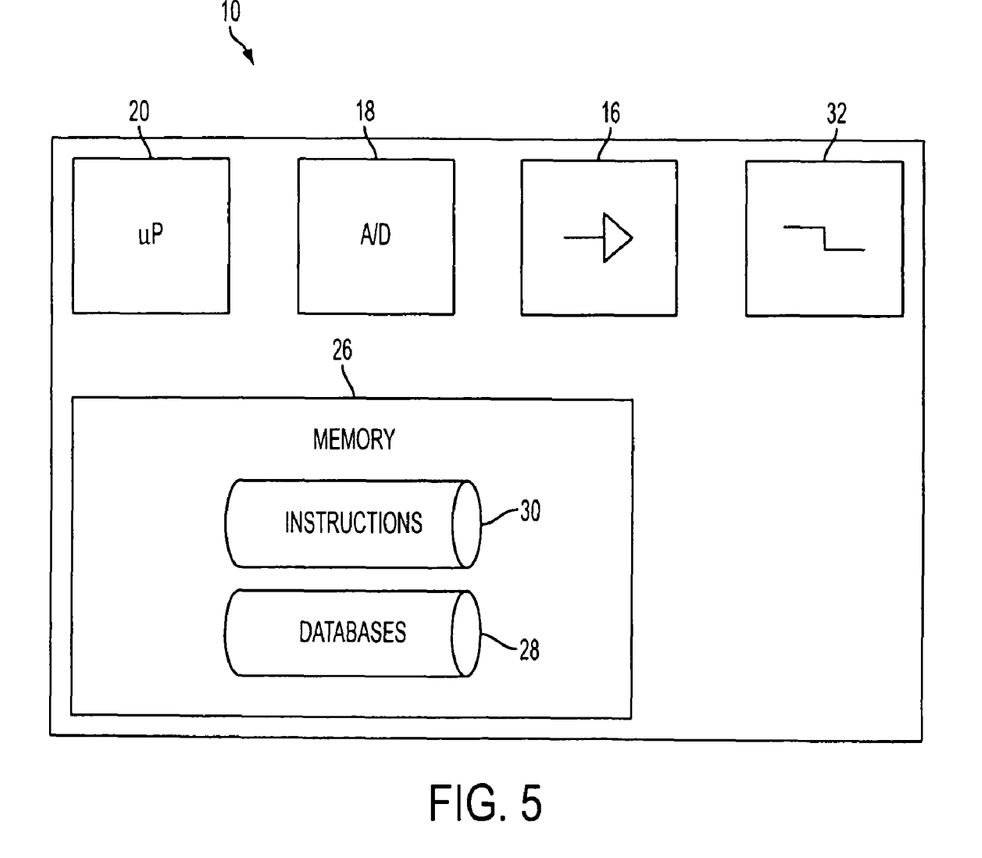
FIG. 5 is a somewhat schematic view of a seizure monitoring system in accordance with the subject technology.

Referring now to FIG. 5, a somewhat schematic view of the SMDS 10 in accordance with the subject technology is shown. The SMDS 10 is preferably contained in portable housing so that the SMDS 10 can be moved from location to location within a hospital, nursing home and the like. The SMDS 10 would typically have the EEG processor 20 in the same housing as the memory 26. The memory 26 would serve to store a plurality of databases 28. For example, the databases 28 could include the digital data storage 22 and computer file 24 as well as registers, counters and the like as needed during the process 100. The memory 26 would also include sets of instructions 30 for running the process 100 among other functions of the SMDS 10. The SMDS 10 could also include the signal amplifier 16 and analog to digital converter 18 in the same portable housing. The SMDS 10 may also include one or more filters 32 for filtering the EEG signals 12.

The flow chart herein illustrates the structure or the logic of the present technology, possibly as embodied in computer program software or instructions 30 for execution by the SMDS 10. It is envisioned that various electrodes and configuration computers, digital processors or microprocessors can effectively run the present technology. Those skilled in the art will appreciate that the flow chart illustrates the structures of the computer program code elements, including logic circuits on an integrated circuit, that function according to the present technology. As such, the present invention is practiced in its essential embodiments by machine components that render the program code elements in a form that instructs an apparatus to perform a sequence of function steps corresponding to those shown in the flow chart.

Figure 6:
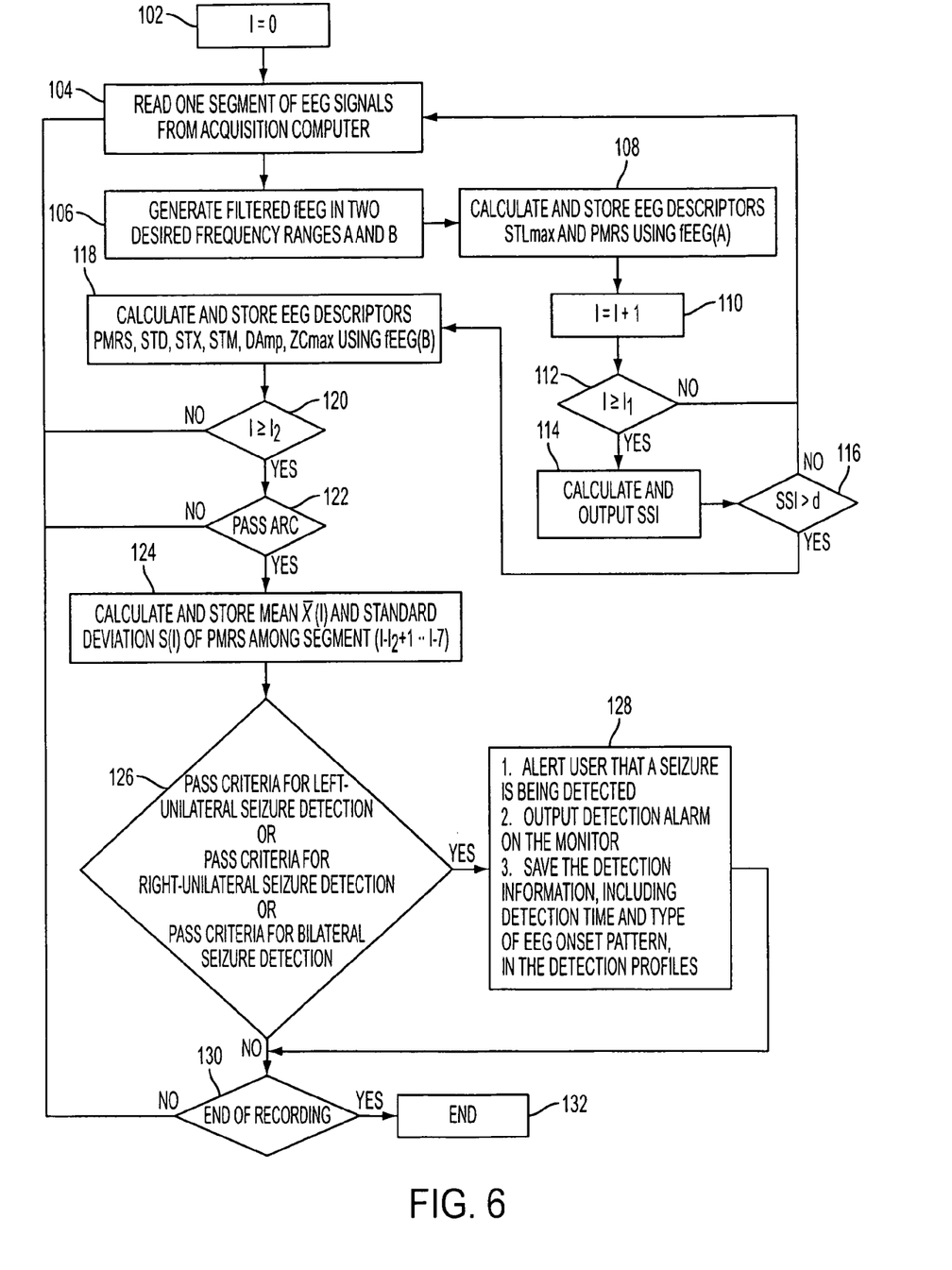
FIG. 6 illustrates a flow chart illustrating an exemplary process for seizure monitoring and detection in accordance with the subject technology.

Referring now to FIG. 6, there is illustrated a flowchart 100 depicting an exemplary process for seizure monitoring and detection using analysis of Electroencephalogram (EEG) signal linear and nonlinear properties. Initially at step 102, the SMDS 10 sets a segment counter to zero (e.g., I=0) and selects a time segment to determine the amounts or segments of information that the SMDS 10 processes. In one embodiment, the time segment is a non-overlapping 5.12 second segment.

At step 104, the SMDS 10 reads one segment of digitized multi-channel signals of an intracranial or scalp EEG recording for analysis. The SMDS 10 can read EEG signals either directly from an EEG acquisition system for real-time monitoring or from pre-recorded EEG signal profiles for post hoc seizure review. For a scalp EEG, a channel of signal is defined as one of a plurality of channel signals of an EEG recording measured across given referential electrodes as illustrated in FIGS. 1A and 1B. Commonly, the referential electrode is located between Cz and Pz (e.g., midline central and parietal regions) as suggested by the American Clinical Neurophysiology Society.

Referring still to FIG. 6, at step 106, the SMDS 10 filters the signal segment in two desired frequency ranges to generate filtered EEG or EEG signals. The two frequency ranges are referred to as filter-A and filter-B so that resulting signals are filter-A EEG signals and filter-B EEG signals. The rationale for the filtering process is to reduce the possibility of false detections caused by the signal artifacts from patients' normal activities. For example, muscle movement, chewing activity, coughing and the like may create false positives. Within the frequency ranges, the information of seizure activity is preserved. In one embodiment, the SMDS 10 uses a Butterworth filter of order 5 with two frequency ranges of approximately 1 to 50 Hz and 1 to 20 Hz for a scalp EEG. For an intracranial EEG, the SMDS 10 may use frequency ranges of approximately 1 to 50 Hz and 1 to 35 Hz. The SMDS 10 applies the filtering procedure to each of the EEG channels analyzed.

At step 108, the SMDS 10 calculates non-linear EEG descriptors of the filter-A EEG signals. One acceptable approach to calculate non-linear EEG descriptors for each signal channel is to estimate characteristics such as the complexity, chaoticity, stationarity, or regularity of the reconstructed p-dimensional state space.

A preferred embodiment of the SMDS 10 calculates non-linear EEG descriptors, 7-dimensional short-term maximum Lyapunov exponents (STLmax) and a 3-dimensional pattern match regularity statistics (PMRS). These non-linear EEG descriptors are used to quantify the spatio-temporal dynamics of the multi-channel EEG signals. One acceptable approach to calculate the STLmax descriptors is described below:

STLmax estimates the signal stability in a re-constructed multi-dimensional state space. The parameters associated with the state space re-construction are the embedding dimension p and time delay $\tau$. It will be understood that the actual value of p and $\tau$ may depend upon which descriptors are being relied upon to measure the non-linear properties of each channel. For example, with regard to STLmax, the SMDS 10 may use p equal to seven (7) and $\tau$ equal to 10 to 20 milliseconds to capture the dynamic characteristics of the spatio-temporal response associated with a given channel. With such a parameter setting, EEG signals during a seizure exhibit lower STLmax values (typically between 2 and 3), compared to the interictal (typically between 3 and 8) and the postictal (typically between 8 and 10) values. In addition, it is often observed that STLmax values among EEG channels gradually converge before the occurrence of a seizure. The timing of this convergence varies across patients, or even across seizures in the same patient. Typically, the convergence ranges from 10 minutes to 120 minutes before a seizure onset.

After the state space re-construction, STLmax is then computed for each EEG channel. In one embodiment, the SMDS 10 uses the iterative selection of pairs of points on the state space and the estimation of the convergence/divergence of the respective trajectory over time. More specifically, the largest Lyapunov exponent (Lmax or L1) is defined as the average of local Lyapunov exponents $L_{ij}$ in the state space, that is:

$$L_{max} = \frac{1}{N} \cdot \sum_{N} L_{ij},$$

where N is the necessary number of iterations for the convergence of the Lmax estimated from a data segment of n points (n=N·Δt), and $$L_{ij} = \frac{1}{\Delta t} \cdot \log_2 \frac{|Y(t_i + \Delta t) - Y(t_j + \Delta t)|}{|Y(t_i) - Y(t_j)|},$$

where Δt is the evolution time allowed for the vector difference $\delta_0(x_{ij})=|Y(t_i)-Y(t_j)|$ to evolve to the new difference $\delta_\kappa(x_k)=|Y(t_i+\Delta t)-Y(t_j+\Delta t)|$, where Δt=k·dt and dt is the sampling period of the data u(t). If Δt is given in seconds, Lmax is in bits/sec.

PMRS is utilized to quantify the regularity of an EEG based on the signal patterns. PMRS estimates the likelihood of pattern similarity and/or stationary parts for a given time series. PMRS can be applied to detect EEG state changes such as seizures. Major advantages of PMRS include that PMRS can be interpreted in both stochastic and chaotic models as well as fast computation. The steps to calculate PMRS include re-construction of state vectors, searching for the pattern matched state vectors, and the estimation of pattern match probabilities. Specially, given an EEG signal U={$u_1$, $u_2$, ..., $u_n$}, let $\hat{\sigma}_u$ be the standard deviation of U For a given integer m (embedding dimension), reconstruct state vectors of U as $x_i$={$u_i$, $u_{i+1}$, ..., $u_{i+m-1}$}, 1≤i≤n-m+1, then for a given positive real number r (typically r=0.2$_u$), $x_i$ and $x_j$ are considered pattern matched to each other if:

|$u_i-u_j$|<r, |$u_{i+m-1}-u_{j+m-1}$|<r, and sign($u_{i+k}-u_{i+k-1}$)=sign($u_{j+k}-u_{j+k-1}$) for 1≤k≤m-1 Then $$PMRS = -\frac{1}{n-m}\sum_{i=1}^{n-m} \ln(\hat{p}_i),$$

where
$p_i$=Pr{sign($u_{i+m}-u_{i+m-1}$)=sign($u_{j+m}-u_{j+m-1}$)|$x_i$ and $x_j$ are pattern matched}

Similar to the calculation of STLmax, PMRS may be calculated for each sequential 5.12 second, non-overlapping EEG segment for each channel. Typically, the PMRS values drop significantly from those of during the preceding baseline period during the seizure and move back to the higher values immediately after the seizure ends. A typical PMRS value during a seizure EEG segment ranges from 0.3 to 0.4, while the PMRS ranges between 0.5 to 0.7 for EEG segments during non-seizure, waking, and artifact-free periods. These observations suggest that the EEG signal during the ictal period is less complex than other periods and that the signal during the interictal or postictal period is more complex.

After the SMDS 10 calculates the nonlinear EEG descriptors, the SMDS 10 saves and stores the profiles in a pre-determined folder in the memory (e.g., a computer drive). The profiles can be used for post hoc EEG analysis. At step 110, the SMDS 10 increases the segment counter I by one (1).

At step 112, the SMDS 10 checks whether the segment counter I is greater than or equal to a preset number of segments ($I_1$). $I_1$ is a pre-determined number of segments required for estimating the seizure susceptibility index (SSI). It is understood that $I_1$ may depend upon which descriptors are being relied upon to measure the spatio-temporal properties of the selected critical groups of channels. For example, if the segment counter I is greater than or equal to sixty with $I_1$ set to sixty (60), the SMDS 10 will proceed to step 114, otherwise, the SMDS 10 returns to step 104 to again read and analyze the next segment of EEG so that the segment counter I continues to be increased until the SMDS 10 passes to step 114.

At step 114, the SMDS 10 calculates and stores a SSI (block 114). SSI is a probability measure between 0 and 1 that represents the likelihood of an impending seizure. Since the SMDS 10 is substantially based on the dynamical descriptors of EEG, SSI will be generated in real-time in a form of probability index by analyzing the distribution of dynamic descriptors. SSI not only can be used as a real-time seizure monitoring index, but also can be utilized as a pre-filtered criterion for real-time seizure detection system. Exemplary embodiments of SSI include the following approaches.

Inverse T-index Based SSI

A T-index time series may be utilized as a seizure warning descriptor or to calculate an SSI. Thus, an inverse probability of a T-index may be used as a SSI. T-index is calculated as T= $\sqrt{n}\cdot\bar{d}/\hat{\sigma}_d$, where $\bar{d}$ and $\hat{\sigma}_d$ are the sample mean value and standard deviation of the differences in STLmax values between two EEG channels. Under the null hypothesis: Mean STLmax values of two EEG channels are identical, T is distributed as t distribution with n−1 degrees of freedom. Based on this statistical property, after obtaining T-index value, an inverse-T SSI will be calculated simultaneously (with very short delay because of fast PC computation) as $2\cdot(1-T_{n-1}^{-1})$. This inverse-T SSI will be outputted in real-time as indication of how likely a seizure will occur. Larger value suggests that the patient is in greater risk of having a seizure.

STLmax Distribution Based SSI

A STLmax distribution based SSI may be calculated. STLmax measures how ordered an EEG signal is. STLmax drops to the lowest values during the ictal period (i.e., the time period with the most risk at seizure) and rises back to the highest values postictally (i.e., the time period with the least risk at seizure). These behaviors in STLmax time series allow the use of the distribution of STLmax values during the interictal and preictal periods. Without being limited to any particular theory, when a patient is at risk of seizure, the STLmax values will move more and more outside the distribution of interictal STLmax values, at least for some EEG channels. Therefore, to generate a STLmax distribution-based SSI is to estimate the distribution density of STLmax values during the entire time period excluding ictal and postictal periods. Preferably, the distribution is estimated for each EEG channel. Therefore, the distribution-based SSI can be output in real-time for each EEG channel. Alternatively, a signal SSI can be output as the proportion of EEG channels that exhibit STLmax values outside 95% confidence interval derived from the estimated distributions. Since EEG channels represent the spatial distribution of a brain, such an SSI could be used as a brain function index indicating the percentage of the brain regions that are generating abnormal electrical activities over time compared to seizure-free time periods. As a result, a higher SSI value would suggest that the patient is at greater risk of having a seizure.

Dynamical Entrainment Based SSI

A dynamical entrainment based SSI may be calculated. Most of the EEG channel pairs exhibit dynamic entrainment during the ictal period, and very few pairs are entrained after the seizure. Thus, a SSI based on the estimated probability that an EEG channel pair is dynamically entrained may be used. The entrainment of an EEG channel pair will be determined by the T-index of STLmax values. When the T-index is below a certain confidence threshold based on the statistical T-distribution, the pair is considered as entrained. The entrainment analysis may be performed on each EEG channel pair and the dynamical entrainment based SSI can be the proportion of EEG channel pairs that exhibit entrainment. As a result, when the SSI is close to 1, the patient is at great risk of having a seizure, and when close to 0, the patient is not likely to have a seizure.

Still referring to FIG. 3, the SMDS 10 can use one or more of the methods to determine an SSI. In one embodiment, the SMDS 10 calculates multiple SSI and determines an average. At step 116, before the SMDS 10 performs the seizure detection steps, the SMDS 10 first checks the value of the calculated SSI. If the SSI is not large enough, the SMDS 10 returns to step 104 and reads and analyzes the next segment of EEG. If SSI is large enough, the SMDS 10 proceeds to the seizure detection process starting at step 118. The threshold (d) for the SSI in step 116 is user selected. The threshold (d) is set to serve as a pre-screening step for seizure detection and selected accordingly. For example, a threshold may be set at SSI=0.5 for a given patient that is most likely in an interictal state when SSI<0.5. However, if the SSI is to be used for seizure warning application, the threshold (d) may be increased to reduce the false warning rate. For example, a threshold may be set at SSI=0.8 for a given patient that is most likely experiencing a preictal state when SSI>0.8.

While the PMRS and STLmax are very sensitive to the seizure EEG patterns, there are other patterns that may exhibit similar values of STLmax and PMRS because of the rhythmic activities, and therefore could cause false detections. In order to reject these false detections, after the SMDS 10 passes the SSI criterion at step 116, the SMDS 10 calculates another PMRS, referred as PMRS-B, and linear signal properties primarily based on the amplitude and frequency of the filter-B EEG at step 118.

At step 118, the SMDS 10 calculates the PMRS-B using the filter-B signal (i.e., the lower frequency band compared with filter-A) in the seizure detection analysis so that the signals have less effects from high-frequency artifacts such as muscle and chewing activity.

The SMDS 10 may calculate signal deviation (STD), local maximum and minimum signal deviation (STX and STM, respectively), maximum high-low frequency amplitude difference (DAmp), and the maximum zero crossing frequency (ZCmax). STD is simply the sample standard deviation of the signal amplitude within the calculation window. In one embodiment, STX calculates the maximum 1 second standard deviation within the calculation window. STM calculates the minimum 1 second standard deviation within the calculation window. ZCmax estimates the maximum one second frequency of the one-directional zero crossing within the calculation window. DAmp calculates the maximum difference of signal amplitude between the 70 Hz filtered signal and the 20 Hz filtered signal within the calculation window. The STD and STX can reject the false detections caused by the muscle activity, significant movement activity, electrode artifacts, and recording system artifacts. The STM, the difference between STX and STM, and DAmp can reject false detections caused by certain sleep patterns. ZCmax can serve as an additional rule for rejecting detections caused by signal patterns with high frequency and signal patters with highly rhythmic and seizure-like amplitude. Further, an EEG segment may be rejected as a seizure segment if the ZCmax of the monitoring channel is greater than 13, or its STD value is greater than 80 µV with signal gain of approximately 0.9 µV per bit. A user may determine various thresholds and criteria, and enter the information into the SMDS 10 for automatic application.

After completion of step 118, the SMDS 10 proceeds to step 120 to determine if a statistically sufficient sample size or number ($I_2$) of segments has been acquired for the calculation of the mean and standard deviation of the background signal dynamics in step 124. The SMDS 10 assesses if the sample size is large enough by making the comparison $I \geq I_2$. If the segment counter I is less than $I_2$, the SMDS 10 goes back to step 104 and reads and analyzes the next segment of EEG. If the segment counter I is equal to or greater than $I_2$, the SMDS 10 proceeds to step 122 to calculate an artifact rejection criteria (ARC). Since sixty (60) data points is usually considered statistically sufficient to estimate a sample mean and a sample standard deviation with great confidence, in one embodiment, $I_2$ is at least sixty-six (66). In other words, in order for the process to proceed to step 122, the counter segment I has to be least sixty-six (66). The reason to have six (6) data points between the baseline period and the present segment is to reduce the time correlation between the baseline period and the present segment when comparing EEG descriptors (e.g., PMRS-B) in detecting seizures.

Artifact Rejection Criteria (ARC)

Based on the above EEG descriptors calculated in step 118, a set of ARC are calculated at step 122. The ARC filter the data to prevent false positives, false negatives, and the like by examining each EEG segment in the range to determine whether or not the EEG segment should be rejected from use in the sample range. For a first ARC, the SMDS 10 rejects an EEG segment as a seizure segment if the percentage of channel pairs that exhibit similar PMRS-B values is high. This type of artifact is generally due to recording system error that most of the recording channels exhibit similar signal regularity. An exemplary threshold or percentage for this criterion is 0.45%, with a difference of PMRS-B value between two EEG channels<0.03.

For a second ARC, the SMDS 10 rejects an EEG segment as a seizure segment if the percentage of channel pairs that exhibit similar STD values is high. This type of artifact is generally due to recording system error that most of the recording channels exhibit similar signal amplitude. An exemplary threshold for this criterion is 0.50%, with a difference of STD value between two EEG channels<5 µV with signal gain of approximately 0.9 µV per bit.

For a third ARC, the SMDS 10 rejects an EEG segment as a seizure segment if any of the preceding few segments exhibits abnormally high mean STD value across all the channels processed. This type of high-amplitude artifact across all EEG channels sometimes results in high regularity for the following EEG signals. An exemplary threshold for this criterion is 500 µV, with signal gain at approximately 0.9 µV per bit, for any of the preceding three (3) segments.

For a fourth ARC, the SMDS 10 rejects an EEG segment as a seizure segment if the number of EEG channels exhibiting both low PMRS-B values and low STM values is high. This type of artifact is generally due to a normal sleep EEG pattern. An exemplary threshold for this criterion is at least 7 channels exhibit PMRS-B values<0.4 and STM<25 µV with signal gain at approximately 0.9 µV per bit.

For a fifth ARC, the SMDS 10 rejects an EEG segment as a seizure segment if the number of EEG channels exhibiting low DAmp values is high in the temporal and occipital regions. This type of artifact is also due to a normal sleep EEG pattern. An exemplary threshold for this criterion is all temporal and occipital channels (O1, O2, F7, F8, T3, T4, T5, and T6) exhibit DAmp<25 µV with signal gain at approximately 0.9 µV per bit.

For a sixth ARC, the SMDS 10 rejects an EEG segment as a seizure segment if the difference of PMRS-B values between the occipital and temporal regions is large. This type of artifact is generally due to a normal sleep EEG pattern. An exemplary threshold for this criterion is 0.1.

Comparisons based on the PMRS-B values for the selected EEG channels indicate that PMRS-B values may decrease significantly at the seizure onset. One of the most important criteria for the SMDS 10 is that the PMRS-B values for the selected EEG channels decrease significantly at the seizure onset. The detection of these decreases needs a statistical threshold for comparison.

In one embodiment, the SMDS 10 calculates a combination of sample mean ($\bar{x}$) and sample standard deviation (s) of the previous values (for example, a preceding 5 minute interval), such as ($\bar{x} - c \cdot s$), where c is a constant variable. It is worth noting that in order to reduce the correlation between this threshold and the current value, this previous time interval should end at least 5 segments (approximately 25 seconds) before the current segment. In addition, to reduce the effects from signal artifacts to the baseline values, the PMRS-B values are automatically adjusted to a preset "seizure-free" value (=0.6) if the corresponding ZCmax or STD values exceed the preset thresholds. In a preferred embodiment, the system segment counter should be at least equal to 67 in order to calculate this threshold, and this is determined at step 120 ($I > I_2$). If the segment counter I is less than $I_2$, the SMDS 10 goes back to step 104 and reads and analyzes the next segment of EEG. If the segment counter I is larger than $I_2$, the SMDS 10 calculates the threshold for comparison, as described at step 124.

After determining this detection threshold at step 126, the SMDS 10 then compares the current EEG descriptors with three sets of criteria for detecting a seizure event as well as determining the type of EEG seizure onset. The types of EEG seizure onset may be classified as follows: (1) left-unilateral EEG seizure onset; (2) right-unilateral EEG seizure onset; and (3) bilateral EEG seizure onset.

Left-unilateral Seizure Onset

Detection criteria for a left-unilateral seizure onset are preferably based on segments that have passed the ARC. A first left-unilateral seizure onset criteria is that the PMRS-B from the primary left side channel of the present and next segments must be significantly smaller than the mean PMRS-B value in the same channel during the earlier baseline interval. In one embodiment, this baseline interval consists of 60 data segments from "present segment—65" to "present segment—6", a preceding time interval that allows a 5 data point interval between the present segment and a respective baseline interval as noted above with respect to steps 118-122. The rationale for this criterion is to detect the highly regular EEG signals during the ictal period. An exemplary threshold for this criterion is mean baseline PMRS-B value minus 2.5 times the baseline standard deviation. In a preferred embodiment, this primary left side channel can be F7, T3, or T5.

A second left-unilateral seizure onset criteria is that the PMRS-B from the primary and secondary left side channels of the present segment must be significantly smaller than the PMRS-B from their homologous contralateral channels for the same segment. The rationale for this criterion is that, for a left-unilateral seizure onset, the EEG signals from the left side channels become regular earlier than their homologous contralateral channels. An exemplary difference for this criterion is 0.05. In a preferred embodiment, a combination of primary and secondary left side channels can be (F7, T3), (T3, T5), or (T5, T3).

A third left-unilateral seizure onset criteria is that the PMRS-B values from the primary and secondary left side channels at the present segment must be smaller than a threshold. The rationale for this criterion is that, during a left-unilateral seizure, the EEG signals from the primary and secondary left side channels must have a high degree of regularity. Therefore, the threshold should be based on the distribution of the baseline (interictal) PMRS values. An exemplary threshold for this criterion is 0.45.

A fourth left-unilateral seizure onset criteria is that the unadjusted PMRS-B value from the primary or the secondary left side channel at the next segment must be smaller than a threshold. This criterion is to increase the confidence of the detection. Same as the previous criterion, this threshold should be based on the distribution of the baseline (interictal) PMRS values. An exemplary threshold for this criterion is 0.45.

A fifth left-unilateral seizure onset criteria is that the PMRS-B value from the primary or secondary homologous contralateral channel at the present segment must be larger than a threshold. This criterion is to reduce the chance that the detection is due to a sleep EEG pattern. Therefore, this threshold should be based on the distribution of the PMRS values of EEG signals during the sleep activities. An exemplary threshold for this criterion is 0.35.

A sixth left-unilateral seizure onset criteria is that the PMRS-B value from the left or right occipital channel must be smaller than a threshold. This criterion is to reduce the chance that the detection is due to a recording electrode artifact. Therefore, this threshold should be based on the distribution of the PMRS values of EEG signals during the sleep activities. An exemplary threshold for this criterion is 0.55.

A seventh left-unilateral seizure onset criteria is that the STX value from the primary left side channel and its homologous contralateral channel at the present segment must be smaller than a threshold. This criterion is to reduce the chance that the detection is due to a recording electrode artifact. Therefore, this threshold should be based on the distribution of the STX values of EEG signals during recording artifact activities. An exemplary threshold for this criterion is 80 µV with signal gain at approximately 0.9 µV per bit.

An eight left-unilateral seizure onset criteria is that the STX value from the secondary left side channel and its homologous contralateral channel at the present segment must be smaller than a threshold. This criterion is to reduce the chance that the detection is due to a recording electrode artifact. Therefore, this threshold should be based on the distribution of the STX values of EEG signals during recording artifact activities. An exemplary threshold for this criterion is 80 µV with signal gain at approximately 0.9 µV per bit.

A ninth left-unilateral seizure onset criteria is that the ZCmax value from the primary and secondary left side channels must be smaller than a threshold. This criterion is to reduce the chance that the detection is due to a muscle and/or chewing activity artifact. Therefore, this threshold should be based on the distribution of the ZCmax values of EEG signals during muscle and chewing activities. An exemplary threshold for this criterion is 14.

A tenth left-unilateral seizure onset criteria is that the mean STD values of left and right frontal polar channels at the present and/or next segment must be larger than a threshold. This tenth criterion is to reduce the chance that the detection is due to a sleep EEG pattern with no eye movement activity. Therefore, this threshold should be based on the distribution of the STD values of frontal polar EEG signals during waking state with vertical eye movements. An exemplary threshold for this criterion is 15 μV with signal gain at approximately 0.9 μV per bit.

An eleventh left-unilateral seizure onset criteria is that the mean STD values among the left side channels must be smaller than a threshold. This eleventh criterion is to reduce the chance that the detection is due to a recording electrode artifact. Therefore, this threshold should be based on the distribution of the mean STD values of the left-side EEG signals during recording electrode artifacts. An exemplary threshold for this criterion is 80 μV with signal gain approximately at 0.9 μV per bit.

A twelfth left-unilateral seizure onset criteria is that the mean STD values among the left side channels must be larger than the mean STD value among the right side channels. This criterion is to reduce the chance that the detection is due to a sleep EEG pattern or a recording system artifact.

A thirteenth left-unilateral seizure onset criteria is that the ratio of the STD value of the primary left side channel to its homologous contralateral channel must be greater then a threshold. This thirteenth criterion is to reduce the chance that the detection is due to a sleep EEG pattern. Therefore, this threshold should be based on the distribution of the STD ratio of homologous left and right EEG channels during sleep activities. An exemplary threshold for this criterion is 1.25 (25% larger). Preferably, the SMDS 10 uses all the ARC criteria for evaluation.

Right-unilateral Seizure Onset

Detection criteria for a right-unilateral seizure onset are preferably based on segments that have passed the ARC. A first right-unilateral seizure onset criteria is that the PMRS-B from the primary right side channel of the present and next segments must be significantly smaller than the mean PMRS-B value in the same channel during the earlier baseline interval. In one embodiment, this baseline interval consists of 60 data segments from "present segment—65" to "present segment—6", a preceding time interval that allows a 5 data point interval between the present segment and a respective baseline interval as noted above with respect to steps 118-122. The rationale for this criterion is to detect the highly regular EEG signals during the ictal period. An exemplary threshold for this criterion is mean PMRS-B value minuses 2.5 of the standard deviation. In a preferred embodiment, this primary left side channel can be F8, T4, or T6.

A second right-unilateral seizure onset criteria is that the PMRS-B from the primary and secondary right side channels of the present segment must be significantly smaller than the PMRS-B from their homologous contralateral channels for the same segment. The rationale for this criterion is that, for a right-unilateral seizure onset, the EEG signals from the right side channels become regular earlier than their homologous contralateral channels. An exemplary difference for this criterion is 0.05. In a preferred embodiment, a combination of primary and secondary left side channels can be (F8, T4), (T4, T6), or (T6, T4).

A third right-unilateral seizure onset criteria is that the PMRS-B values from the primary and secondary right side channels at the present segment must be smaller than a threshold. The rationale for this criterion is that, during a right-unilateral seizure, the EEG signals from the primary and secondary right side channels must have a high degree of regularity. Thus, the threshold should be based on the distribution of the baseline interictal PMRS values. An exemplary threshold for this criterion is 0.45.

A fourth right-unilateral seizure onset criteria is that the unadjusted PMRS-B value from the primary or the secondary right side channel at the next segment must be smaller than a threshold. This criterion is to increase the confidence of the detection. Same as the previous criterion, this threshold should be based on the distribution of the baseline interictal PMRS values. An exemplary threshold for this criterion is 0.45.

A fifth right-unilateral seizure onset criteria is that the PMRS-B value from the primary or secondary homologous contralateral channel at the present segment must be larger than threshold. This criterion is to reduce the chance that the detection is due to a sleep EEG pattern. Thus, the threshold should be based on the distribution of the PMRS values of EEG signals during the sleep activities. An exemplary threshold for this criterion is 0.35.

A sixth right-unilateral seizure onset criteria is that the PMRS-B value from the left or right occipital channel must be smaller than a threshold. This criterion is to reduce the chance that the detection is due to a recording electrode artifact. Thus, the threshold should be based on the distribution of the PMRS values of EEG signals during sleep activities. An exemplary threshold for this criterion is 0.55.

A seventh right-unilateral seizure onset criteria is that the STX value from the primary right side channel and its homologous contralateral channel at the present segment must be smaller than a threshold. This criterion is to reduce the chance that the detection is due to a recording electrode artifact. Thus, the threshold should be based on the distribution of the STX values of EEG signals during recording artifact activities. An exemplary threshold for this criterion is 80 μV with signal gain at approximately 0.9 μV per bit.

A eighth right-unilateral seizure onset criteria is that the STX value from the secondary right side channel and its homologous contralateral channel at the present segment must be smaller than a threshold. This criterion is to reduce the chance that the detection is due to a recording electrode artifact. Thus, the threshold should be based on the distribution of the STX values of EEG signals during recording artifact activities. An exemplary threshold for this criterion is 80 μV with signal gain at approximately 0.9 μV per bit.

A ninth right-unilateral seizure onset criteria is that the ZCmax value from the primary and secondary right side channels must be smaller than a threshold. This criterion is to reduce the chance that the detection is due to a muscle and/or chewing activity artifact. Thus, the threshold should be based on the distribution of the Zcmax values of EEG signals during muscle and chewing activities. An exemplary threshold for this criterion is 14.

A tenth right-unilateral seizure onset criteria is that the mean STD values of left and right frontal polar channels at the present and/or next segment must be larger than a threshold. This criterion is to reduce the chance that the detection is due to a sleep EEG pattern with no eye movement activity. Thus, the threshold should be based on the distribution of the STD values of frontal polar EEG signals during a waking state with vertical eye movements. An exemplary threshold for this criterion is 15 μV with signal gain at approximately 0.9 μV per bit.

An eleventh right-unilateral seizure onset criteria is that the mean STD values among the right side channels must be smaller than a threshold. This criterion is to reduce the chance that the detection is due to a recording electrode artifact. Thus, the threshold should be based on the distribution of mean STD values of the left-side EEG signals during recording electrode artifacts. An exemplary threshold for this criterion is 80 μV with signal gain at approximately 0.9 μV per bit.

A twelfth right-unilateral seizure onset criteria is that the mean STD values among the right side channels must be larger than the mean STD value among the right side channels. This criterion is to reduce the chance that the detection is due to a sleep EEG pattern or a recording system artifact.

A thirteenth right-unilateral seizure onset criteria is that the ratio of the STD value of the primary left side channel to its homologous contralateral channel must be greater then a threshold. This criterion is to reduce the chance that the detection is due to a sleep EEG pattern. Thus, the threshold should be based on the distribution of the STD ratio of homologous left and right EEG channels during sleep activities. An exemplary threshold for this criterion is 1.25 times or 25% larger. Preferably, all thirteen criteria with ARC are used for the best detection of seizure activity.

Bi-lateral Seizure Onset

Detection criteria for a bi-lateral seizure onset are preferably based on segments that have passed the ARC. A first bi-lateral seizure onset criteria is that there are a sufficient number of channels exhibiting small PMRS-B values with a proper range of ZCmax values at the present and next segments, and with a proper range of STX values at the present segment. The rationale for this criterion is to identify segments with signal characteristics of ictal EEG signals. Therefore, same as in the unilateral seizure onset detection, these thresholds should be determined based on the distributions of PMRS-B, ZCmax, and STX values during seizure-free interictal periods. An exemplary threshold for number of channels is 4 among temporal and occipital channels, with PMRS-B<0.45, ZCmax<14, and STX<80 μV with signal gain at approximately 0.9 μV per bit. Similar criterion can be used simultaneously to increase detection specificity with number of channels is 3, with PMRS-B<0.40, ZCmax<14, and STX<80 μV with signal gain at approximately 0.9 μV per bit.

A second bi-lateral seizure onset criteria is that there is a sufficient number of channels exhibiting significant reduction in PMRS-B values at the present segment, when compared to the mean PMRS-B value in the same channel during the earlier baseline interval. In one embodiment, this baseline interval consists of 60 data segments from "present segment—65" to "present segment—6", a preceding time interval that allows a 5 data point interval between the present segment and a respective baseline interval as noted above with respect to steps 118-122. The rationale for this criterion is to detect the highly regular EEG signals during the ictal period. An exemplary threshold for this criterion is at least 3 channels among temporal and occipital channels that exhibit present PMRS-B values smaller than their baseline mean PMRS-B value minuses 2.5 times the baseline standard deviation.

A third bi-lateral seizure onset criteria is that the mean difference of STD values at the present segment between left side and right side channels must be smaller than a threshold. This criterion is based on the characteristic that, unlike unilateral seizures, a bi-lateral ictal EEG activities change from its baseline on both side almost at the same time. Therefore, this threshold should be based on the distribution of the mean STD difference between left and right EEG channels during a bilateral seizure. An exemplary threshold for this criterion is 20 μV with signal gain at approximately 0.9 μV per bit.

A fourth bi-lateral seizure onset criteria is that the mean STD values among the monitored channels at the present and next segments must be great than a threshold. The criterion is to reduce the chance that the detection is due to a sleep EEG pattern with bilaterally small signal amplitudes. Therefore, this threshold should be based on the distribution of the mean STD among monitored EEG channels during sleep activities. An exemplary threshold for this criterion is 20 μV with signal gain at approximately 0.9 μV per bit.

A fifth bi-lateral seizure onset criteria is that the mean STD values of left and right frontal polar channels at the present and/or next segment must be larger than a threshold. This criterion is to reduce the chance that the detection is due to a sleep EEG pattern with no eye movement activity. Therefore, this threshold should be based on the distribution of the STD values of frontal polar EEG signals during waking state with vertical eye movements. An exemplary threshold for this criterion is 15 μV with signal gain at approximately 0.9 μV per bit. Again, it is envisioned that using all criteria with ARC provides enhanced performance.

After a seizure is detected in step 126, the SMDS 10 proceed to steps 128. It is envisioned that the SMDS 10 can also sequentially process evaluating left, right and bilateral seizure detection criteria. At step 128, the SMDS 10 may (1) alert the user(s) that a seizure is being detected, (2) output a seizure alarm on the EEG monitor, and/or (3) save the detection information including the detection time and type of EEG seizure onset in the profile for post hoc analysis. After the detection process is finished for the current segment (e.g., completion of step 126), the SMDS 10 may check if the recording is ended at step 130. If the recording is finished, which is determined by observing if the remaining EEG data is sufficient for a calculation segment, the process 100 passes to step 132, where the process 100 ends. If the recording is not finished, the SMDS 10 returns to step 104 and reads and analyzes the next segment of EEG.

It will be appreciated by those of ordinary skill in the pertinent art that the functions of several elements may, in alternative embodiments, be carried out by fewer elements, or a single element. Similarly, in some embodiments, any functional element may perform fewer, or different, operations than those described with respect to the illustrated embodiment. Also, functional elements (e.g., counters, modules, databases, interfaces, computers, servers and the like) shown as distinct for purposes of illustration may be incorporated within other functional elements in a particular implementation.

While the invention has been described with respect to preferred embodiments, those skilled in the art will readily appreciate that various changes and/or modifications can be made to the invention without departing from the spirit or scope of the invention as defined by the appended claims.

What is claimed is:

1. A system for monitoring brain pathological conditions and detecting critical neurological events of a patient in real time from a series of analyses on scalp or intracranial brain electrical activity, such as multi-channel EEG signals, comprising:
   a. an amplifier configured to receive and amplify the EEG signals;
   b. an analog-to-digital multi-converter configured to convert the EEG signals into digital signals;
   c. a signal processor configured to process the digital signals and to provide outputs indicative of the brain pathological conditions, wherein the processor is programmed to perform analyses for each EEG channel as follows:
- 1.c-1. filter signals in a first frequency range A and a second frequency range B, each frequency range including a plurality of segments;
- 1.c-2. for each segment in the first frequency range A, calculate nonlinear EEG descriptors that extract signal characteristics, wherein the nonlinear EEG descriptors include short-term maximum Lyapunov exponent (STLmax) and pattern match regularity statistic (PMRS-A) and additionally include descriptors selected from the group consisting of correlation dimension, entropy, mutual information and combinations thereof;
- 1.c-3. calculate a convergence measure of the nonlinear EEG descriptors among selected EEG channels for each sequential segment;
- 1.c-4. calculate a seizure susceptibility index (SSI) based on a distribution of STLmax, and PMRS as well as respective convergence measures T-index$_1$ and T-index$_2$ outputs;
- 1.c-5. determine whether an impending seizure is susceptible based on SSI values; and
- 1.c-6. when the impending seizure is indicated, perform the following: i) for each segment in the second frequency range B, calculate a pattern match regularity statistic (PMRS-B); ii) for each segment in the second frequency range B, calculate the standard deviation of the signal amplitude (STD); iii) for each segment in the second frequency range B, calculate a maximum and minimum one second standard deviation of a signal amplitude (STX and STM); iv) for each segment in the second frequency range B, calculate a maximum one-second negative-to-positive zero-crossing frequency, where each one second signal is normalized to have mean zero (ZCmax); v) for sequential EEG segments, calculate the maximum amplitude difference between a low and a high frequency band (DAmp); and vi) determine whether a seizure event is occurring based on PMRS-B, STD, STX, STM, DAmp, and ZCmax outputs.

2. The system of claim 1, wherein the processor is further operative to determine an EEG onset type selected from the group consisting of a left-unilateral onset, a right-unilateral onset, and a bilateral onset.

3. The system of claim 1, wherein the processor is further operative to use pair-t statistic as convergence measure.

4. The system of claim 1, wherein each segment is a non-overlapping EEG segment for calculating the signal descriptors.

5. The system of claim 1, wherein overlapping signal descriptors are used for estimating the respective convergence measures among the selected EEG channels.

6. The system of claim 1, wherein a digital filter is utilized to filter the EEG signals.

7. The method in claim 6, wherein the digital filter is a $5^{th}$ order Butterworth filter with frequency ranges in A of approximately 1 to 50 Hz and B of approximately 1 to 20 Hz for scalp EEG signals.

8. The method in claim 6, wherein the digital filter is a $5^{th}$ order Butterworth filter with frequency ranges in A of approximately 1 to 50 Hz and B of approximately 1 to 35 Hz for intracranial EEG signals.

9. The system of claim 1, wherein STLmax and PMRS EEG descriptors are calculated using an embedding dimension of p and time delay of τ for state vector construction.

10. The system of claim 9, wherein the processor uses an embedding dimension and time delay of approximately 10 ms for state vector construction for calculating STLmax EEG descriptor.

11. The system of claim 1, wherein the SSI is a probability index ranged from 0 to 1.

12. The system of claim 1, wherein the SSI is calculated as the inverse of T-index$_1$ according to a T distribution with corresponding degrees of freedom.

13. The system of claim 1, wherein the SSI is calculated as a proportion of channel pairs that exhibit T-index$_1$ values smaller than a statistical threshold with a preset significance level α.

14. The system of claim 1, wherein the processor is further operative to calculate a PMRS EEG descriptor using an embedding dimension and time delay of approximately 2.5 ms for state vector construction.

15. The system of claim 1, wherein the SSI is calculated based on the distribution function of PMRS-A and convergence and divergence of PMRS-A values among the selected EEG channels.

16. The system of claim 1, wherein the SSI is calculated as the proportion of EEG channels that exhibit abnormal PMRS-A values compared to the PMRS-A distribution function during seizure-free periods.

17. The system of claim 1, wherein the SSI is calculated as the inverse of T-index$_2$ according to the T distribution with the corresponding degrees of freedom.

18. The system of claim 1, wherein the SSI is calculated as the proportion of channel pairs that exhibit T-index$_2$ values smaller than a statistical threshold with a preset significance level α.

19. The system of claim 1, wherein the SSI is calculated based on a distribution function of STLmax convergence, and the convergence and divergence properties of STLmax values among the selected EEG channels.

20. The system of claim 1, wherein the SSI is calculated as a proportion of EEG channels that exhibit abnormal STLmax values compared to the STLmax distribution function during seizure-free periods.

21. The system of claim 1, wherein the PMRS-B value of an EEG channel of segment T is automatically adjusted to a preset "seizure-free" value if its corresponding ZCmax or STD values excess preset thresholds.

22. The system of claim 1, wherein a segment T is automatically rejected as a seizure segment if a percentage of channel pairs that exhibit close PMRS-B values is high.

23. The system of claim 1, wherein a segment T is automatically rejected as a seizure segment if the percentage of channel pairs that exhibit close STD values is high.

24. The system of claim 1, wherein a segment T is automatically rejected as a seizure segment if any of the preceding few segments exhibits abnormally high mean STD value across all the channels processed.

25. The system of claim 1, wherein a segment T is automatically rejected as a seizure segment if a sleep EEG pattern is detected.

26. The system of claim 25, wherein a sleep pattern is defined quantitatively as a large number of EEG channels exhibiting both low PMRS-B values and low STM values.

27. The system of claim 25, wherein a sleep pattern is defined quantitatively as a large number of EEG channels exhibiting low DAmp values.

28. The system of claim 25, wherein a sleep pattern is defined quantitatively as a large difference of PMRS-B values between the occipital and temporal regions.

29. The system of claim 1, wherein the processor is further operative to make a determination at segment T for a left-unilateral-onset seizure event occurrence based criteria that involve signal regularity of a selected primary and secondary left-side channels and comparisons of signal regularity between left and side channels.

30. The system of claim 29, selection of the primary and secondary left side channels includes (F7, T3), (T3, T5) and (T5, T3) for detecting temporal lobe seizures.

31. The system of claim 30, wherein: the PMRS-B from the primary left side channel at segments T and T+1 must be significantly smaller than a mean PMRS-B value in the same channel during the earlier baseline interval; the PMRS-B from the primary left side channel at segment T must be smaller than the PMRS-B, with a certain degree, from a homologous contralateral channel at segment T; the PMRS-B from the secondary left side channel at segment T must be smaller than the PMRS-B, with a certain degree, from a homologous contralateral channel at segment T; the PMRS-B from the primary left side channel at segment T must be smaller than a threshold; the PMRS-B from the secondary left side channel at segment T must be smaller than a threshold; the unadjusted PMRS-B value from the primary or the secondary left side channel at segment T+1 must be smaller than a threshold; the PMRS-B value from the primary or secondary homologous contralateral channel at segment T must be larger than a threshold; the PMRS-B value from the left or right occipital channel must be smaller than a threshold; the STX value from the primary left side channel and its homologous contralateral channel at segment T must be smaller than a threshold; the STX value from the secondary left side channel and its homologous contralateral channel at segment T must be smaller than a threshold; the ZCmax value from the primary left side channel must be smaller than a threshold; the ZCmax value from the secondary left side channel must be smaller than a threshold;

the mean STD values of left and right frontal polar channels at segment T and/or T+1 must be larger than a threshold; the mean STD values among the left side channels must be smaller than a threshold; the mean STD values among the left side channels must be larger than the mean STD value among the right side channels; and the ratio of the STD value of the primary left side channel to a respective homologous contralateral channel must be greater than a threshold.

32. The system of claim 1, wherein the processor is further operative to make determination at segment T for a right-unilateral-onset seizure event occurrence based on criteria that involve signal regularity of the selected primary and secondary right-side channels and comparisons of signal regularity between left and side channels.

33. The system of claim 32, wherein the selections of primary and secondary right side channels include (F8, T4), (T4, T6), and (T6, T4) for detecting temporal lobe seizures.

34. The system of claim 32, wherein: the PMRS-B from the primary right side channel at segments T and T+1 must be significantly smaller than a mean PMRS-B value in the same channel during the earlier baseline interval; the PMRS-B from the primary right side channel at segment T must be smaller than the PMRS-B, with a certain degree, from a homologous contralateral channel at segment T; the PMRS-B from the secondary right side channel at segment T must be smaller than the PMRS-B, with a certain degree, from a homologous contralateral channel at segment T; the PMRS-B from the primary right side channel at segment T must be smaller than a threshold; the PMRS-B from the secondary right side channel at segment T must be smaller than a threshold; an unadjusted PMRS-B value from the primary or the secondary right side channel at segment T+1 must be smaller than a threshold; the PMRS-B value from the primary or secondary homologous contralateral channel at segment T must be larger than a threshold; the PMRS-B value from the left or right occipital channel must be smaller than a threshold; the STX value from the primary right side channel and its homologous contralateral channel at segment T must be smaller than a threshold; the STX value from the secondary right side channel and its homologous contralateral channel at segment T must be smaller than a threshold; the ZCmax value from the primary right side channel must be smaller than a threshold; the ZCmax value from the secondary right side channel must be smaller than a threshold; the mean STD values of left and right frontal polar channels at segment T and/or T+1 must be larger than a threshold; the mean STD values among the right side channels must be smaller than a threshold; the mean STD values among the right side channels must be larger than the mean STD value among the left side channels; and a ratio of the STD value of the primary right side channel to a respective homologous contralateral channel must be greater than a threshold.

35. The system of claim 1, wherein a determination at segment T for a bilateral-onset seizure event occurrence is based on the following conditions on selected channels: a sufficient number of channels exhibiting small PMRS-B values with a proper range of ZCmax values at segments T and T+1, and a proper range of STX values at segment T; a sufficient number of channels exhibiting significant reduction in PMRS-B values at segment T, when compared to the mean PMRS-B value in the same channel during an earlier baseline interval; a mean difference of STD values at segment T between left and right channels must be smaller than a threshold; a mean STD values among the monitored channels at segments T and T+1 must be great than a threshold; and STD values from left and right frontal polar channels at segments T and T+1 must be larger than a threshold.

36. The system of claim 1, wherein monitoring of seizures is conducted in conditions selected from the group consisting of Epilepsy Monitoring Unit conditions, Intensive Care Unit conditions, ambulatory conditions and emergency conditions.

37. The system of claim 1, wherein scalp brain electrical activity, such as the EEG signals are taken from electrodes placed directly on the brain to record electrical activity directly from the cerebral cortex of a patient.

* * * * *